(12) United States Patent
Yamaki et al.

(10) Patent No.: US 6,686,028 B2
(45) Date of Patent: Feb. 3, 2004

(54) HYDROPHILIC ELASTICALLY STRETCHABLE COMPOSITE SHEET

(75) Inventors: Koichi Yamaki, Kagawa-ken (JP); Satoshi Mitsuno, Kagawa-ken (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 09/942,722

(22) Filed: Aug. 31, 2001

(65) Prior Publication Data

US 2002/0028324 A1 Mar. 7, 2002

(30) Foreign Application Priority Data

Sep. 1, 2000  (JP) .......................................... 2000-266296

(51) Int. Cl.[7] .............................................. B32B 27/14
(52) U.S. Cl. ........................ 428/198; 428/196; 428/78; 428/369; 428/370; 428/371
(58) Field of Search ................... 428/197, 236, 428/246, 255, 78, 198, 365, 364, 369, 370, 359, 196

(56) References Cited

U.S. PATENT DOCUMENTS 5,681,645 A  * 10/1997  Strack et al. ............... 428/196

FOREIGN PATENT DOCUMENTS

| EP | 1 069 223 | 1/2001 |
| JP | 6-184897 | 7/1994 |
| JP | 8-504693 | 5/1996 |
| WO | WO 96/38620 | 12/1996 |

* cited by examiner

Primary Examiner—Merrick Dixon
(74) Attorney, Agent, or Firm—Lowe Hauptman Gilman & Berner LLP

(57) ABSTRACT

A hydrophilic elastically stretchable composite sheet composed of an elastically stretchable first sheet and an inelastically stretchable second sheet intermittently bonded to at least one surface of the first sheet. At least one of the first sheet and the second sheet contains hydrophilic material. The composite sheet has a high sweat absorbability.

20 Claims, 1 Drawing Sheet

HYDROPHILIC ELASTICALLY STRETCHABLE COMPOSITE SHEET

BACKGROUND OF THE INVENTION

This invention relates to an elastically stretchable composite sheet containing hydrophilic material.

Japanese Patent Application Publication No. 1994-184897A and Japanese Patent Application (PCT) Publication No. 1996-504693 describe an elastically stretchable composite sheet comprising an elastic sheet having stretchability and a sheet-like fibrous assembly having inelastic stretchability bonded together. The presence of the fibrous assembly enables such a composite sheet to offer a flexible touch desired for a topsheet in a wearing article such as a disposable diaper or a sanitary napkin.

The composite sheet of prior art advantageously eliminates a rubber touch possibly experienced by a wearer as the elastic sheet comes in contact with the wearer's skin and offers a cloth-like touch. However, the fibrous assembly constituting the composite sheet is formed, for example, with long fibers obtained through the melt spinning process or by microfibers obtained through the melt blown process. The composite sheet of prior art is disadvantageous in that these fibers are not sweat-absorbent.

SUMMARY OF THE INVENTION

It is an object of this invention to provide an elastically stretchable composite sheet with cloth-like touch and sweat-absorbability and thereby to improve feeling to wear a wearing article using this composite sheet.

According to this invention, there is provided an elastically stretchable composite sheet having a X- and Y-directions orthogonal to each other and comprising a first sheet adapted to be elastically stretchable at least in the Y-direction and a second sheet formed with fibrous assembly adapted to be inelastically stretchable in the Y-direction and bonded to at least one surface of the first sheet.

The improvement according to this invention is in that the first and second sheets are bonded together in bonding zones arranged intermittently in the Y-direction wherein each section of the fiber forming the second sheet extending between each pair of the adjacent bonding zones is longer than a straight distance between the pair of the adjacent bonding zones and at least one of the first and second sheets contains hydrophilic material.

DETAILED DESCRIPTION OF THE PREFERRED EMBODIMENTS

Figure 1:
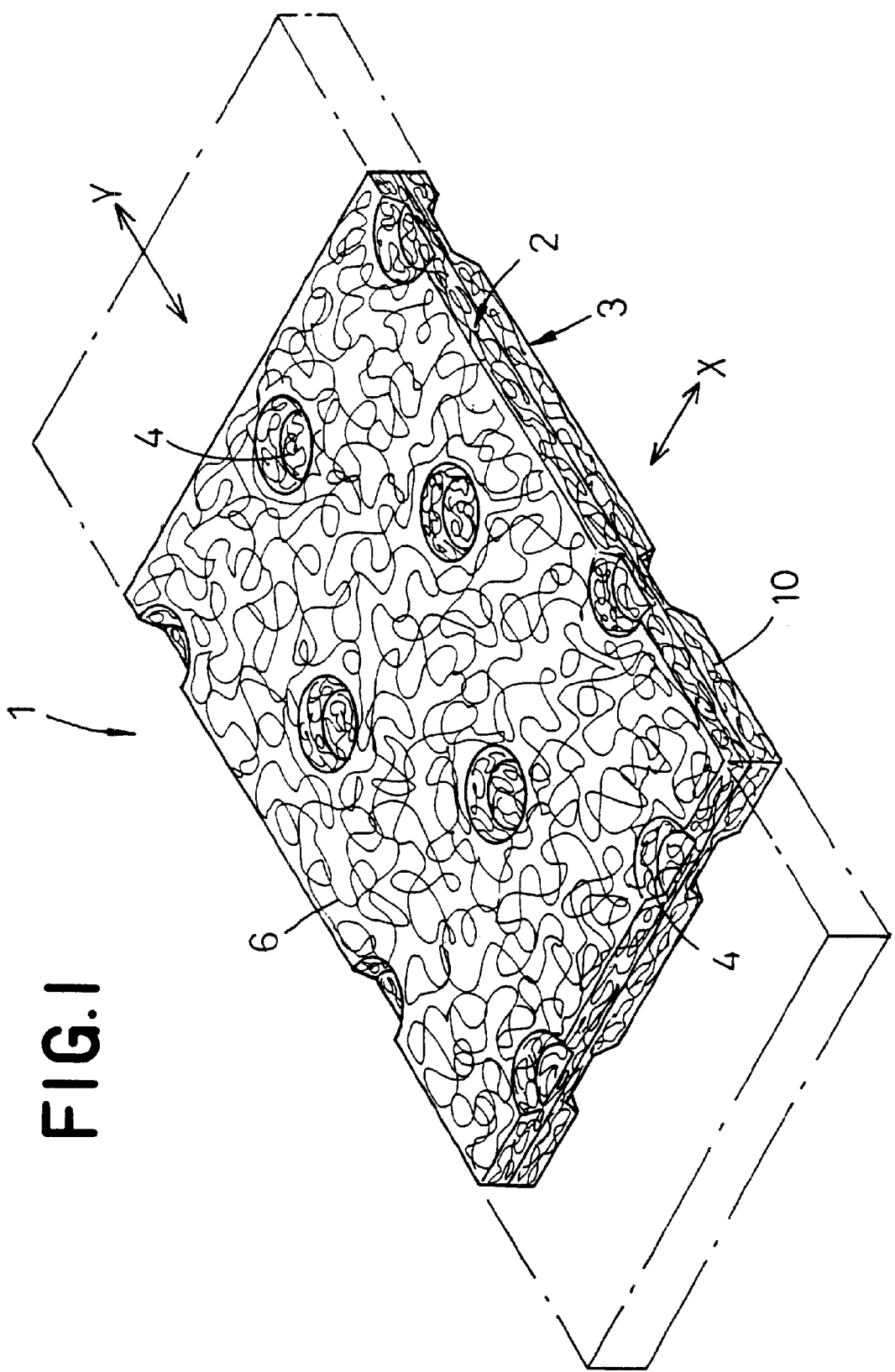
FIG. 1 is a perspective view showing a composite sheet according to this invention.

Details of a elastically stretchable composite sheet containing hydrophilic material will be more fully understood from the description given hereunder with reference to the accompanying drawings.

An elastically stretchable composite sheet 1 containing hydrophilic material shown by FIG. 1 in a perspective view is suitable as a liquid-pervious or liquid-impervious topsheet used for a disposable wearing article such as a disposable diaper, a sanitary napkin or a disposable gown adapted to be used in medical site. This composite sheet 1 comprises an upper layer 2 and a lower layer 3 welded together in bonding zones 4. The composite sheet 1 is elastically stretchable preferably in X- and Y-directions orthogonal to each other or at least in the Y-direction as indicated by chain lines.

The upper layer 2 of the composite sheet 1 is inelastically stretchable preferably in the X- and Y-directions or at least in the Y-direction. This upper layer 2 is formed with an assembly of fibers 6 extending at least between a pair of the bonding zones 4, 4. Such fibers 6 may be short fibers, preferably long fibers, more preferably continuous fibers. Each of these fibers 6 extending between a pair of the bonding zones 4, 4 is longer than a straight distance between these two bonding zones 4, 4 and describes an irregular curve between these bonding zones 4, 4 over the entire upper surface of the lower layer 3. Preferably, the fibers 6 are neither welded nor bonded together, i.e., separated one from another between the bonding zones 4. The upper layer 2 is inelastically stretched and the fibers 6 respectively having described curves between respective pairs of the adjacent bonding zones 4, 4 are reoriented to extend in the Y-direction between these bonding zones 4, 4 as the composite sheet 1 is stretched in the Y-direction.

Such fibers 6 may be, for example, blend of inelastic synthetic resin such as polypropylene, polyester, polyethylene or polypropylene with terpolymer of propylene, ethylene and butene. The fibers 6 may be at least partially incorporated with or coated with hydrophilic material such as sodium alkylsulfonate as hydrophilicity giving agent to make the fibers 6 hydrophilic. Each of the fibers 6 has a diameter preferably of 0.1~50 $\mu$m, more preferably of 0.1~20 $\mu$m and a basis weight preferably of 2~100 $g/m^2$, more preferably of 2~20 $g/m^2$. In the illustrated embodiment, the fibers 6 are provided in the form of continuous fibers treated to become hydrophilic.

The lower layer 3 of the composite sheet 1 is elastically stretchable preferably in both the X-direction and the Y-direction or at least in the Y-direction. The lower layer 3 is stretchable preferably at least by 200%, more preferably by 400% in the Y-direction. After having been stretched by 100%, the lower layer 3 elastically contracts to a length less than 1.3 times its initial length as the lower layer 3 is relieved of the stretching effect. Such lower layer 3 may be formed with an assembly of short fibers, preferably of long fibers, more preferably of continuous fibers wherein these fibers forming such assembly are mechanically entangled or welded together to form a nonwoven fabric, or with a film made of thermoplastic elastomer. These fibers or film may be incorporated with or coated with suitable hydrophilicity giving an agent such as sodium alkylsulfonate to make the lower layer 3 hydrophilic. Such lower layer 3 preferably has a basis weight of 5~200 $g/m^2$. In the illustrated embodiment, the lower layer 3 is formed with continuous fibers 10.

When it is desired that the composite sheet 1 to be used should be breathable, the lower layer 3 preferably presents breathability of at least 10 $cm^3/cm^2 \cdot s$ as measured according to the method A prescribed by §6.27 of JIS L 1096. When it is desired that the composite sheet 1 to be used should be moisture-permeable, the lower layer 3 preferably presents moisture-permeability of at least 1000 $g/m^2/day$ as measured according to the method B prescribed by JIS Z 0208. In combination with such breathable and/or moisture-permeable lower layer 3, it is preferred to use the upper layer 2 having the breathability and/or the moisture-permeability equal to or higher than those of the lower layer 3. Depending on material selection for the upper and lower layers 2, 3, it is possible to make the composite sheet 1 liquid-pervious or liquid-impervious.

The bonding zones 4 may be arranged intermittently at least in the Y-direction of X- and Y-directions. The upper and lower layers 2, 3 be bonded to each other by heating them together under a pressure or using a supersonic sealing technique. It is also possible to unite the fibers 6 of the upper layer 2 and the fibers 10 of the lower layer 3 using a needle punching or high pressure columnar water jet treatment. Each of the bonding zones 4 has an area of 0.03~10 mm$^2$ and a total area of these bonding zones 4 is preferably 1~50% of the composite sheet's total area.

Pulling such composite sheet 1 in the Y-direction causes the lower layer 3 to be elastically stretched in the Y-direction and this stretching of the lower layer 3 causes, in turn, the fibers 6 of the upper layer 2 describing the curves to be reoriented and to be inelastically stretched in the Y-direction. A force required to stretch the composite sheet 1 is substantially equal to force required to stretch the lower layer 3 before the curves described by the fibers 6 are completely straightened. In the upper layer 2, the fibers 6 are merely reoriented and therefore substantially do not affect the force required to stretch the composite sheet 1. The fibers 6 are completely straightened between the respective pairs of the adjacent bonding zones 4, 4 as the composite sheet 1 is further stretched. Further stretching of the composite sheet 1 from such state requires the force required to stretch the lower layer 3 plus the force required to stretch the fibers 6 having already been straightened. The fibers 6 presenting such behavior preferably describe loops on the upper surface of the composite sheet 1 so that the upper layer 2 is stretchable not only in the Y-direction but also in the X-direction.

On the upper layer 2 of the composite sheet 1, the fibers 6 describe curves overlapping one another and some of the fibers 6 extend to curve upward from the composite sheet 1 so that the upper layer 2 as a whole offers soft cloth-like touch. In this upper layer 2, interstices of the fibers 6 assist good breathability. In addition, the fibers 6 are at least partially hydrophilic and offer good sweat-absorbability as they come in contact with the wearer's skin. The fibers 6 having absorbed a certain amount of sweat can be rapidly dried as a plenty of air passing through the interstices of these fibers 6. The wearing article using such composite sheet 1 is advantageous in its soft touch, high breathability as well as high absorbing and drying rate for sweat so far as the upper layer 2 used to lie on body side. The composite sheet 1 may be used as stock material for the wearing article in the manner that both the upper layer 2 and the lower layer 3 are hydrophilic or the upper layer 2 is hydrophilic while the lower layer 3 is hydrophobic. However, depending on its purpose of use, it is possible to use the composite sheet 1 in the manner that the upper layer 2 is hydrophobic while the lower layer 3 is hydrophilic.

To exploit this invention, the fibers 6 of the upper layer 2 is not limited to the thermoplastic synthetic fibers treated to become hydrophilic, but may be hydrophilic regenerated fibers or natural fibers such as rayon, cotton, silk or jute fibers. Alternatively, both the fibers 6 of the upper layer 2 and the fibers 10 of the lower layer 3 may comprise mixture of hydrophilic and hydrophobic fibers. In such case, the hydrophilic fibers include also pulp fibers. This invention may be also implemented in a manner that the lower layer 3 of the composite sheet 1 shown in FIG. 1 is provided on its lower surface also with the inelastically stretchable fibrous assembly similar to the upper layer 2. This additional fibrous assembly may contain hydrophilic fibers or not contain such hydrophilic fibers.

In the composite sheet according to this invention, any one of the elastically stretchable sheet and the inelastically stretchable fibrous assembly sheet bonded to at least one surface of the elastically stretchable sheet contains hydrophilic material so that the wearing article using this composite sheet may offer soft touch, high breathability and sweat-absorbability.

What is claimed is:

1. An elastically stretchable composite sheet, comprising:
   an elastic web having a stretchability in at least one direction; first sheet adapted to be elastically stretchable at least in said Y-direction and
   an inelastic web made of non-textile material comprising component fibers, said inelastic web having an inelastic extensibility in said direction and being bonded to at least one surface of said elastic web, wherein:
   said elastic and inelastic webs are bonded together in bonding zones arranged intermittently in said direction;
   sections of the component fibers extending between each pair of the adjacent bonding zones are longer than a straight distance between said pair of the adjacent bonding zones; and
   at least one of said elastic and inelastic webs contains hydrophilic material.

2. The composite sheet according to claim 1, wherein said elastic web comprises elastically stretchable thermoplastic synthetic fibers.

3. The composite sheet according to claim 1, wherein said elastic web comprises elastically stretchable thermoplastic synthetic resin film.

4. The composite sheet according to claim 1, wherein said hydrophilic material comprises hydrophilic fibers.

5. The composite sheet according to claim 1, wherein said hydrophilic material comprises hydrophilicity giving agent that coats said at least one of said elastic and inelastic webs.

6. The composite sheet according to claim 1, wherein said hydrophilic material comprises hydrophilicity giving agent that is incorporated into said at least one of said elastic and inelastic webs.

7. The composite sheet according to claim 1, wherein said elastic and inelastic webs are breathable and moisture-pervious.

8. The composite sheet according to claim 1, wherein at least one of said elastic and inelastic webs is liquid-impervious.

9. The composite sheet according to claim 1, wherein said component fibers are neither sealed nor bonded with one another in bond-free regions between said bonding zones.

10. The composite sheet according to claim 9, wherein said component fibers are separated one from another in said bond-free regions.

11. The composite sheet according to claim 1, wherein said component fibers describe loops in said bond-free regions.

12. The composite sheet according to claim 1, wherein said component fibers are continuous fibers.

13. The composite sheet according to claim 3, wherein said film is moisture-permeable.

14. A composite sheet, comprising:
   an elastically stretchable web; and
   an inelastically extensible web comprising component fibers that are arranged randomly, rather than in an identifiable pattern, in said inelastically extensible web; wherein
   said inelastically extensible web is intermittently bonded to at least one surface of said elastically stretchable web; and
   at least one of said elastically stretchable and inelastically extensible webs contains hydrophilic material.

15. The composite sheet according to claim 14, wherein said component fibers continuously in extending and describing curves in bonding-free regions of said composite sheet where said elastically extensible web is not bonded to said elastically stretchable web.

16. The composite sheet according to claim 14, wherein said composite sheet consists essentially of said elastically stretchable web and said inelastically extensible web.

17. The composite sheet according to claim 1, wherein said composite sheet consists essentially of said elastic web and said inelastic web.

18. The composite sheet according to claim 14, wherein said elastically stretchable web is a film.

19. The composite sheet according to claim 14, wherein said webs are configured so that said sheet is liquid-pervious.

20. The composite sheet according to claim 14, wherein said elastically stretchable web is hydrophilic and said inelastically extensible web is hydrophobic.

* * * * *